United States Patent [19]

Legay et al.

[11] Patent Number: 5,702,424
[45] Date of Patent: Dec. 30, 1997

[54] METHOD AND APPARATUS FOR CONTROLLING THE CHANGE OF AN ESCAPE INTERVAL IN AN ACTIVE IMPLANTABLE MEDICAL DEVICE

[75] Inventors: Thierry Legay, Fontenay Les Briis; Jean-Luc Bonnet, Vanves; Laurence Geroux, Plessis Robinson, all of France

[73] Assignee: ELA Medical S.A., Montrouge, France

[21] Appl. No.: 657,802

[22] Filed: May 31, 1996

[30] Foreign Application Priority Data

May 31, 1995 [FR] France .................. 95 06476

[51] Int. Cl.[6] ........................ A61N 1/362
[52] U.S. Cl. ........................ 607/9
[58] Field of Search ............... 607/9, 14, 25

[56] References Cited

U.S. PATENT DOCUMENTS

| | | | |
|---|---|---|---|
| 3,693,626 | 9/1972 | Cole. | |
| 4,941,471 | 7/1990 | Mehra | 607/9 |
| 5,271,394 | 12/1993 | Girodo et al. | 607/15 |
| 5,330,513 | 7/1994 | Nichols et al. | 607/32 |
| 5,527,347 | 6/1996 | Shelton et al. | 607/9 |
| 5,534,017 | 7/1996 | van Krieken et al. | 607/14 |

FOREIGN PATENT DOCUMENTS

| | | | |
|---|---|---|---|
| 488841 | 11/1991 | European Pat. Off. | A61N 1/368 |
| 647454 | 4/1995 | European Pat. Off. | A61N 1/365 |
| 92/03182 | 3/1992 | WIPO | A61N 1/365 |
| 93/16756 | 9/1993 | WIPO | A61N 1/365 |

Primary Examiner—William E. Kamm
Assistant Examiner—George R. Evanisko
Attorney, Agent, or Firm—Orrick, Herrington & Sutcliffe LLP

[57] ABSTRACT

An active implantable medical device, notably a cardiac pacemaker or fibrillator, which detects the instantaneous cardiac rhythm, spontaneous or stimulated, of the bearer of the device, and delivers stimulation pulses with a variable escape interval and which increases gradually this escape interval. The gradual increase of the escape interval is obtained by memorizing information corresponding to the evolution of the cardiac rhythm sensed by a conventional detection circuit over a first time period, wherein the escape interval to be adjusted is later in time to the memorized information, notably by determining a variable rate of increase of the escape interval, which variable rate is essentially determined as a function of the memorized information, and/or by operating an integration of the previously detected cardiac rhythm.

40 Claims, 7 Drawing Sheets

FIG_1

FIG_2

FIG_3

FIG_4

FIG_5

FIG_6

| EIF | THRESHctr |
|---|---|
| 926-1000ms | 31 |
| 851-925ms | 63 |
| 776-850ms | 95 |
| 701-775ms | 127 |
| 626-700ms | 159 |
| 551-625ms | 191 |
| 476-550ms | 223 |
| 400-475ms | 255 |

FIG_7

| CTR range | RATEdec |
|---|---|
| 0-31 | 16ms/4cc |
| 32-63 | 8ms/4cc |
| 64-95 | 16ms/12cc |
| 96-127 | 8ms/8cc |
| 128-159 | 8ms/12cc |
| 160-191 | 8ms/16cc |
| 192-223 | 8ms/20cc |
| 224-255 | 8ms/24cc |

FIG_8

METHOD AND APPARATUS FOR CONTROLLING THE CHANGE OF AN ESCAPE INTERVAL IN AN ACTIVE IMPLANTABLE MEDICAL DEVICE

Field of the Invention

The present invention concerns "active implantable medical devices" as those devices are defined by the Directive 90/385/EEC of 20 Jun. 1990 of the of European Economic Community Council, and more particularly cardiac pacemakers and/or defibrillators, whose stimulation frequency can be increased above a base frequency.

BACKGROUND OF THE INVENTION

The first devices of this active implantable type were single chamber demand pacemakers having a smoothing algorithm. A smoothing algorithm allows the stimulation frequency to follow the spontaneous rhythm (i.e., the natural cardiac activity) above of the base frequency, by insuring, in case of the disappearance of the spontaneous rhythm, a continuity in the rhythm by delivering stimulation pulses to produce a stimulation frequency that is gradually decreasing in value until the frequency is reduced to the base frequency. As used herein, the terms "frequency" and "rhythm" are interchangeable.

Others devices of this active implantable type are double chamber pacemakers having atrio-ventricular synchronization. In these devices, the ventricle is normally stimulated according to the spontaneous rhythm of the atrium. In the case of atrial disturbances (extrasystoles, or no atrial event detection), the ventricle is decoupled from the atrium and the stimulation frequency applied to the ventricle is, again, gradually decreased until it reduces to a base or control frequency. The base frequency is typically programmed by a physician. The control frequency is some other limit applied by the device in place of a base frequency.

In the same manner, in more recent active implantable cardiac devices, where the stimulation frequency is "enslaved" to, i.e., determined as a function of, information delivered by one or more sensors (which information is related to the cardiac output requirements of the patient bearing the device), in case of a disappearance of the sensed information or too much of a decrease of the sensed information, the stimulation rhythm has to decrease to a control frequency, without following the information provided by one or more sensors, in a manner that respects the physiology of the patient. In such a device, which also is known as a "rate responsive" device because the stimulation frequency or rate responds to the monitored parameter(s) indicative of the patient's cardiac output requirements, loss of the monitored parameter(s) or a significant reduction in magnitude, e.g., at the end of strenuous physical activity, will produce a change in the stimulation rate that cannot be physiologically tolerated by the patient. Thus, in such a case, a smoothing algorithm is used.

European Patents EP-A-0 488 840 and EP-A-0 488 841 issued to ELA Medical, the assignee of this invention, teach various manners to control the decrease of the cardiac rhythm in these various configurations, for example, by use of deceleration slopes (which are actually defined in milliseconds per cardiac cycle and are implemented to limit the change in magnitude of the escape interval from one cardiac cycle to the next) that are preprogrammed and implemented when the pacemaker machine decides, according to its logic, to institute a return to the base or control frequency, as the case may be.

The parameter of controlling the decrease of the cardiac rhythm also can be defined on the basis of a time of descent between the time when the decrease begins and the time when the programmed base frequency is to be reached.

PCT publication WO-A-93/23115 (to Medtronic) proposes an algorithm of decrease in which the deceleration slopes are calculated based on a parameter that is collected from a physiological sensor, which is supposed to deliver a signal representative of "work", corresponding to the activity of the patient. This management process produces, however, a diminution of the cardiac rhythm that is correlated only to information provided by the sensor (which also presupposes that the pacemaker is of the type enslaved to a physiological parameter (i.e., rate responsive), and has necessarily one or more physiological sensors).

Objects and Summary of the Invention

It is an object of the present invention to propose a solution to the interruption or absence of the rate controlling signals an implantable cardiac pacemaker or defibrillator that is susceptible to decrease the stimulation frequency, in a manner that is better adapted to the patient, according to the parent's previous cardiac rhythm, and, therefore, respecting better the patient's physiological needs.

In others words, in the case of patient effort that is short in duration or of a small increase in magnitude, the system in accordance with the present invention will select a rapid diminution of the stimulation frequency. On the other hand, in the case of violent and/or prolonged patient effort, the system will lengthen the time of descent by applying a less rapid decrease, in a manner to provide to the patient a sufficient recovery time which is better adapted to the patient's real metabolic needs.

It also will be apparent that the invention can be implemented in all types of pacemakers and the like, whether its functioning is enslaved to a sensor (i.e., rate responsive, based on, e.g., activity, acceleration, minute volume, respiration, oxygen saturation, temperature, or any one or more of the parameters known as useful to indicate physiological output requirements). The invention can, therefore, be applied to a complete range of active implantable medical devices, namely pacemakers, including the simplest, because it relies only on the cardiac rhythm, and does not require the collection or processing of externally obtained information. Indeed, as will become clear, the invention may be implemented in an analog and/or digital circuit structure, or a solid state machine and more preferably a microprocessor controlled device having suitable memory and software instructions to implement the logic described below. Suitable pacemakers and defibrillators products which may be modified to implement the invention herein include the products sold under the trade names Opus, Chorus, and Defender, available from the assignee ELA Medical, Montrouge, France.

To this end, one aspect of the present invention is directed to a pacemaker, that is of the type comprising: a detection circuit means which operates to detect the instantaneous cardiac rhythm, whether it is spontaneous (detected) or stimulated (paced), of the bearer the device (i.e., the patient); a stimulation circuit means which operates to deliver stimulation pulses with a variable escape interval; and a circuit means to increase gradually the escape interval, such that the circuit means to increase gradually the escape interval comprises a memory and a circuit means to store information representing the evolution of the cardiac rhythm sensed by the detection circuit means-preceding the present increase of the escape interval (that is, the increase that is about to be made).

In a preferred embodiment, the circuit means to increase gradually the escape interval operates to determine a rate of variable increase of the escape interval, which variable rate is essentially determined as a function of the stored detected cardiac rhythm.

The circuit means to increase gradually the escape interval preferably operates to integrate the cardiac rhythm sensed by the detection circuit means preceding the present increase of the escape interval. More preferably, the circuit means to increase gradually the escape interval operates to increase and decrease a counter, such that the rate of applied increase for the present increase of the escape interval is determined according to the count value reached by this counter.

In this last case, the rate of increase applied to increase the escape interval varies in inversely to the value of the counter. Alternately, the value of the counter may be compared to a series of ranges of predetermined values, each range corresponding to a given value of the rate of applied increase. In yet another embodiment, the authorized variation of the counter is limited between a minimal value and a maximal value, the maximal value being a value that varies as a function of a calculated escape interval value.

Preferably, the speed at which the counter increases varies according to a calculated escape interval value, by applying to the incrementing speed a multiplication factor which varies as a function of the calculated escape interval value.

Preferably also, the speed at which the counter decreases varies according to the interval escape value determined during the preceding cardiac cycle, by applying to the decrementing speed a multiplication factor that varies as a function of the calculated escape interval value.

The present invention also includes a circuit means to determine whether the escape interval is increasing or decreasing, wherein the rate of increase is determined by a processing means to increase gradually the escape interval when a decreasing state is detected, and maintained at the value thus applied so that this state does not change further.

BRIEF DESCRIPTION OF THE DRAWINGS

Other characteristics and advantages of the invention will appear to the person of ordinary skill in the art, in view of the following detailed description of a preferred embodiment of the invention, made with reference to drawings annexed, in which.

DETAILED DESCRIPTION OF THE DRAWINGS

Figure 1:
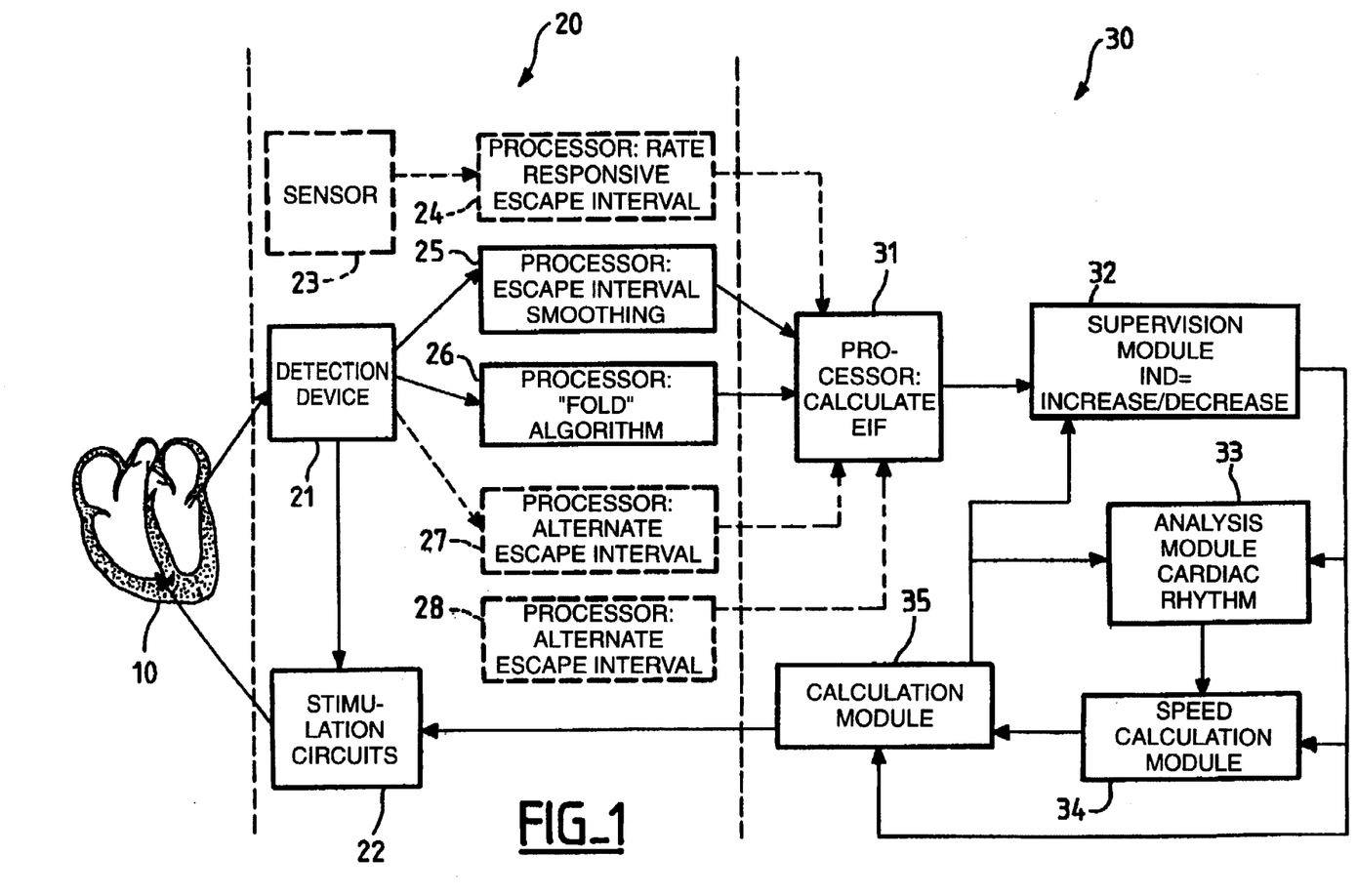
FIG. 1 is a block diagram of an active implantable medical pacemaker device in accordance with a preferred embodiment of the invention.

Referring to FIG. 1, a cardiac pacemaker modified to implement a preferred embodiment of the present invention is illustrated in the form of a block diagram. The pacemaker is represented in the form of two principal blocks, 20 and 30, each composed of an interdependent plurality of modules. The block 20 corresponds to the classic circuits of a cardiac pacemaker, with the optional modules being illustrated in phantom lines. The block 30 corresponds to the modifications of the classic pacemaker in the processing of data (calculations) and in particular to the signal or data processing circuits or modules (depending on whether analog, digital microprocessor or hybrid circuits are used) to implement the present invention.

The heart 10 of the patient produces a spontaneous cardiac rhythm. This rhythm is sensed by a detection module 21 of the classic pacemaker, i.e., the circuits typically used to detect electrical cardiac activity and identify contractions, as a ventricular and/or atrial rhythm, according to whether it concerns a single or multiple chamber pacemaker.

The classic pacemaker device also has a stimulation module 22, which functions to issue a stimulation pulse to the heart based on information determined by processing circuit 30, or is inhibited from delivering automatically a stimulation pulse under the control of the detection module 21, as the case may be.

Optionally, the block 20 comprises one or more sensors 23 (only-one is illustrated) of a physiological parameter, such that a sensor may measure the minute ventilation, the saturation of oxygen in the blood, the temperature, the acceleration (patient motion), etc., in a known manner. In this embodiment, it is also anticipated that a calculation module 24 is provided to determine a stimulation rate responsive escape interval, from the information acquired by the one or more sensors 23. This parameter also is transmitted to the calculation block 30.

The block 20 also includes a calculation module 25, which provides for smoothing the escape interval, using the information of the detection module 21 as described, for example, in EP-A-0 488 841 (Ela Medical) referred to above. This is to prevent paroxystic interruptions of the cardiac rhythm.

It is also anticipated that a calculation module 26 to determine a "fold" escape interval, using the information of the detection module 21, for example, as described in EP-A-0 488 840 (Ela Medical) referred to above or as described in U.S. Pat. No. 5,226,415, to protect the ventricle in response to atrial tachyarrhythmias or extrasystoles in the case of a double chamber pacemaker.

In an alternate embodiment, the block 20 can comprise, in addition, one or more calculation modules 27, 28 to calculate the escape interval on the basis others algorithms which may use information delivered by the detection module 21, as in Module 27, or not use such information, as in Module 28.

The block 30 then, insures the control of stimulation module 22 of the block 20, and comprises a calculation module 31 for calculating the escape interval from data produced by the various modules 25 to 28. Block 30 thus determines a "final" escape interval by combining the results of the various algorithms, which is hereafter designated "EIf", in a manner to best satisfy the physiology and the protection of the patient.

This determined value EIf is applied to a supervision module 32 which discriminates, in a manner described below between the "increase" and "decrease" phases of the cardiac rhythm. This supervision module 32, in turn, controls an analysis module 33, which analyzes the cardiac profile, quantifying increases and decreases of the cardiac rhythm, and a speed calculation module 34, which determines the rate of decrease of the cardiac frequency (which is referred to as "RATEdec") corresponding to the increase of the escape interval that is better adapted to the patient, according to the preceding cardiac rhythm of the patient. This rate of decrease is calculated and set, in the manner indicated hereafter, during each phase of increase of the cardiac rhythm. It is then used during phases of decrease of the cardiac rhythm, which are detected by the supervision module 32.

The block 30 also includes a calculation module 35 which calculates the escape interval applied to the block 20, determining the escape interval of the cardiac cycle under way, at the end of which a stimulation pulse is delivered by the stimulation module 22 if no spontaneous activity is detected by the detection module 21 (or in the opposite case, delivery of the stimulation pulse is inhibited by the detection of spontaneous activity).

Block 30 operates to follow the evolution of the cardiac rhythm and control the decrease of the frequency of stimulation pulses in the following manner. As will be understood, the invention is particularly useful in a microprocessor based device in which the software required to implement the process may be suitably written by a person of ordinary skill in the art.

The following definitions are used hereafter, it being understood that one will refer indifferently to the cardiac or rhythm frequency "f", expressed in $min^{-1}$ or cpm (cycles per minute), the escape interval "EI", expressed in milliseconds, and an increasing frequency corresponds to a decreasing escape interval and vice versa.

The term "Pn−1" refers to the preceding cardiac period and, according to the form of implementation, can be an average of the last x cardiac periods (e.g., x=4) or the preceding cardiac period (e.g., x=1), as appropriate.

The term "EIf" is, as mentioned, the escape interval calculated by one or more algorithms to propose an interval that is equal to or less than the base escape interval. For example, interval EIf can be an interval of enslavement (a rate responsive interval) or a smoothed interval. This interval value concerns the cardiac period "Pn" following the cardiac period Pn−1.

The term "EIn" refers to the escape interval calculated in accordance with the present invention, and concerns the cardiac period Pn.

The term "EIbase" refers to the base stimulation interval and is in general fixed by the physician (e.g., programmed) and is used by the various algorithms of the cardiac pacemaker.

The term "EImin" refers to a minimal interval between successive stimulations, which also is in general fixed by the physician.

The term "EIthresh" refers to an escape interval value threshold that serves to discriminate two different ranges of cardiac periods according to the value of Pn−1 as compared to this threshold. In the present example, EIthresh is arbitrarily fixed to the value of (EIbase+EImin)/2. In other forms of implementation of the invention, one can suppress the notion of threshold interval or, on the contrary, to define not one but several threshold intervals, thereby providing for different behaviors, as will become clear.

The term "RATEdec" previously mentioned concerns the smoothing dynamics during the decrease of the cardiac rhythm and is made by choosing, for each period of decrease of the rhythm, a rate of decrease of the rhythm adapted to the preceding cardiac rhythm of the patient. The algorithm calculates this rate of decrease. In the present example, the rate of decrease RATEdec is calculated in number of milliseconds (ms) per cardiac cycle (cc).

The term "CTR" refers to the count value of a counter that is used to quantify the cardiac profile of the patient. Its present value increases when the cardiac rhythm of the patient accelerates and decreases when the cardiac rhythm of the patient slows. It is the numerical count value CTR of the counter that determines the choice of the rate of declaration RATEdec. In the present example, CTR ranges between 0 and 255.

The term "THRESHCtr" refers to a value limit of the counter for a range of cardiac period datum.

The term "G(EIf)" refers to a function G that determines the value of THRESHCtr as a function of the term EIf. This function is preferably implemented in the form of a table of correspondence (shown in FIG. 6) that attributes a counter limit to each value of EIf. In the present embodiment, it extends between EIbase and EIf and is divided into eight ranges, with each range corresponding to a value THRESHCtr, as set forth in FIG. 6.

The terms "Macc" and "Pacc" refer to variables used to define the manner in which the counter count value CTR is incremented in the course of time. The value Pacc is added to the counter value CTR, and Macc is a multiplier that is in some instances applied to Pacc. In the present example, Pacc=1 and Macc=3.

Similarly, the terms "Mdec" and "Pdec" are variables defining the manner in which the counter count value CTR is decremented over time. The value Pdec is subtracted from the count CTR and Mdec is a multiplier that is applied to Pdec in at least some conditions. In the present example, Pdec=1 and Mdec=3.

Figure 7:
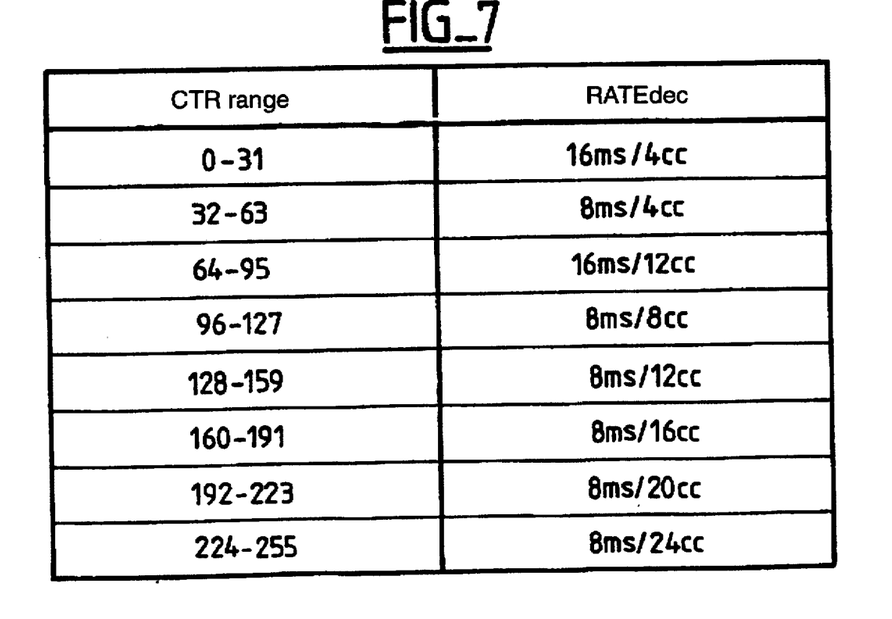
FIG. 7 is a table of values relating the value of the counter and the rate of decrease.

The term F(CTR) is a function that determines the value of RATEdec according to the count value CTR. This function also is preferably implemented as a table of correspondence (shown in FIG. 7) attributing to each value CTR a value RATEdec. In the present example, the table divides the 256 values of counter CTR into eight ranges of 32 values each, and each range corresponds to a given value of RATEdec. For example, for a count value CTR being between 0 and 31, RATEdec is 2 ms/cc, corresponding to the most rapid decrease.

The term "Ind" is a binary indicator that serves to identify the state or phase of the cardiac rhythm, i.e., whether it is increasing or decreasing. The state is determined and used in the algorithm of the invention and can therefore take one of two values, "increase" or "decrease".

The terms "CTRacc" and "nbTHRESHacc" are values used to suppress insignificant variations in accelerations of the stimulated cardiac rhythm. CTRacc ranges between 0 and nbTHRESHacc, and nbTHRESHacc is fixed in the present example to 4.

Similarly, the terms "CTRdec" and "nbTHRESHdec" are values used to suppress insignificant variations of the decelerations of the stimulated cardiac rhythm. CTRdec ranges between 0 and nbTHRESHdec, and nbTHRESHdec is fixed in the present example to 4.

Figure 2:
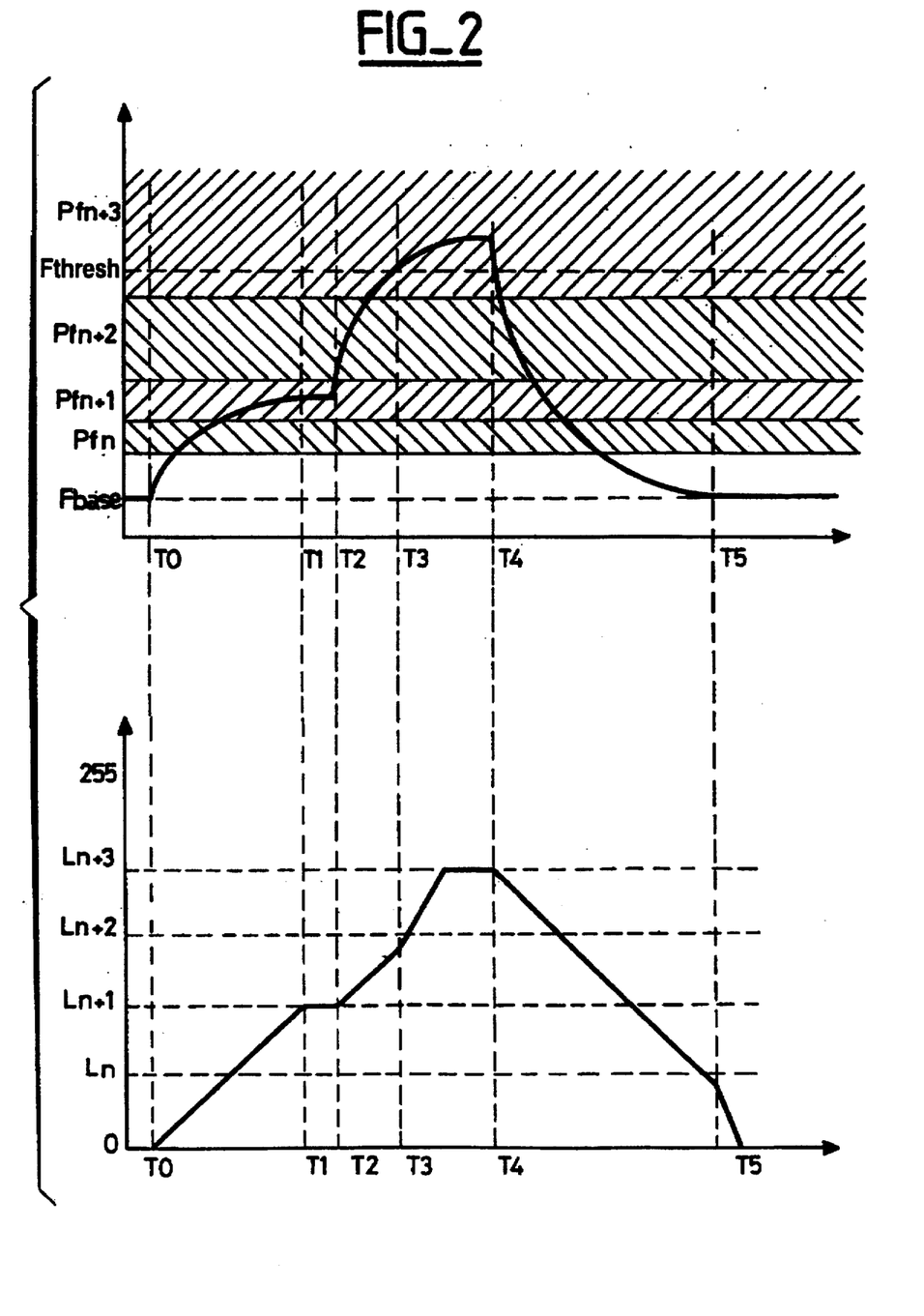
FIG. 2 is a graphical representation of the process of analyzing the cardiac profile, according to the present invention, and the evolution of the cardiac rhythm in a mode to release and control the decrease of the stimulated cardiac rhythm.

Referring now to FIG. 2, the upper portion shows an example of the evolution of the cardiac frequency in response to an "effort" (i.e., a level of patient activity above a resting state) and, the lower portion shows the evolution of the variable CTR, that is to say of the content of the counter which is used to control the variation of the rate of deceleration RATEdec.

If one considers the curve illustrating the evolution of the cardiac frequency, between times T0 and T1, one observes an acceleration of the cardiac rhythm that can be caused by an effort. The cardiac frequency stabilizes gradually, given a constant effort at the increased level (that is, there is a small variation between time T1 and T2). Between time T2 and T4, one observes a resumption of (or an increase in) the effort, with a correlative further acceleration of the cardiac frequency.

It should be understood that these accelerations of the frequency can be the result of spontaneous atrial activity, an algorithm of the cardiac pacemaker, for example, by a rate responsive algorithm, or any other algorithm susceptible to produce an escape interval that is more rapid than the base interval.

Finally, between times T4 and T5, one observes a deceleration of the cardiac rhythm, that can be subsequent to a sinus arrest or loss of signal, as well as to an internal control signal resulting from an algorithm of the pacemaker, for example, a rate responsive algorithm.

In accordance with the invention, this phase of deceleration is controlled to produce an improved physiological condition, that is to say avoiding a deceleration that is too rapid if the preceding effort was a violent (or prolonged) effort and, conversely, a deceleration that is too slow after a brief effort or a low level of effort, in either case not necessitating a long recovery.

The following corresponding terms are noted: "Fbase" is the frequency corresponding to the base interval stimulation EIbase; and "Fthresh" is the frequency corresponding to the threshold interval EIthresh used to discriminate the different ranges of cardiac rhythms, increasing or decreasing.

On the lower part of FIG. 2, the evolution of the counter count value CTR is shown. It increases with the increase of the cardiac rhythm, the details of which will be described more in detail with reference to FIGS. 3 to 6. Essentially, this counter CTR plays a double role, as an integrator and a saturator (trigger switch). The integrator function allows the device to memorize and to analyze the evolution of the cardiac profile (i.e., the function describing the evolution of the cardiac frequency). The saturation function allows the device, by the use of a sequence of thresholds and plateaus that will be described in more detail below, to maintain effectively control of the deceleration to be compatible with the physiology of the patient.

With the cardiac profile example illustrated in FIG. 2, the counter CTR operates the following manner. Before time T0, the patient is at rest having a cardiac frequency at the base frequency Fbase. The counter CTR remains at an initial value that is, e.g., zero.

Between times T0 and T1, the cardiac frequency of the patient increases, while remaining below the threshold valve Fthresh. The value of the counter CTR meter increases regularly by the value Pacc (Macc=1), during this effort. At each new value of the counter CTR, the value of the rate of deceleration RATEdec is determined.

At time T1, the counter CTR reaches the value limit of the counter that corresponds to the current value of the cardiac frequency. This value limit is calculated using the table of correspondence that will be described with respect to FIG. 6. Thus, for a frequency found to be in the range labeled Pfn+1 (FIG. 2), the upper limit of the counter CTR will be Ln+1. The counter count will remain at this value Ln+1 at least until time T2.

Between times T2 and T3, the cardiac frequency resumes its acceleration. The value limit of the counter then changes, since the frequency leaves the range labeled Pfn+1 and the counter continues to increase regularly, by the value Pacc (Macc=1).

At time T3, the cardiac frequency becomes greater than the threshold Fthresh. The counter then increases for each cardiac cycle by the value of the Pacc multiplied by the multiplier Macc (i.e., Macc=3), until the counter CTR to reaches its new limit value-Ln+3.

As shown in FIG. 2, the counter count CTR stabilizes at the limit value Ln+3 until time T4, because the cardiac frequency remains in the range labeled Pfn+3.

At time T4, a decrease of the cardiac rhythm is detected. It is at this point that the algorithm of the present invention manages the calculation of a decreasing stimulation interval.

Figure 6:
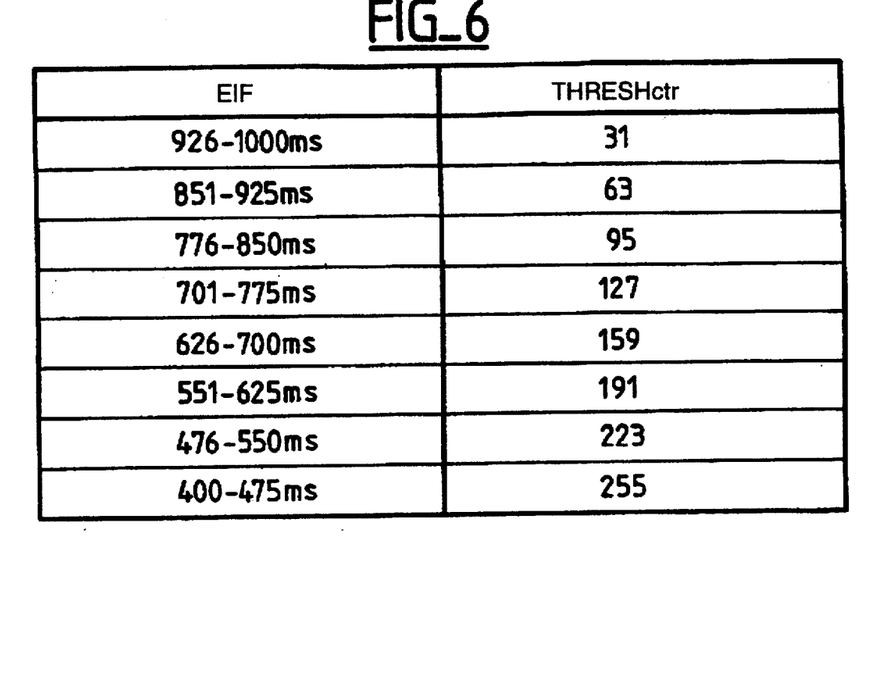
FIG. 6 is a table of values relating the value limits of the counter and the calculated escape interval.

Because the value of the counter is at the limit value Ln+3 at the moment of the decrease, the rate of decrease (RATEdec) chosen for the decrease of the cardiac rhythm after time T4 is the rate of decrease corresponding to the value Ln+3 of the counter, as set forth in the table of correspondence presented in FIG. 6. During the decrease of the cardiac rhythm, the counter will be decremented each cardiac cycle by the value Pdec.

At time T5, the cardiac frequency has reached its base value. The counter will then be decremented more rapidly; it will be decremented by the value Pdec multiplied by a multiplier Mdec each cardiac cycle, until it reaches its initial value, zero.

Figure 3:
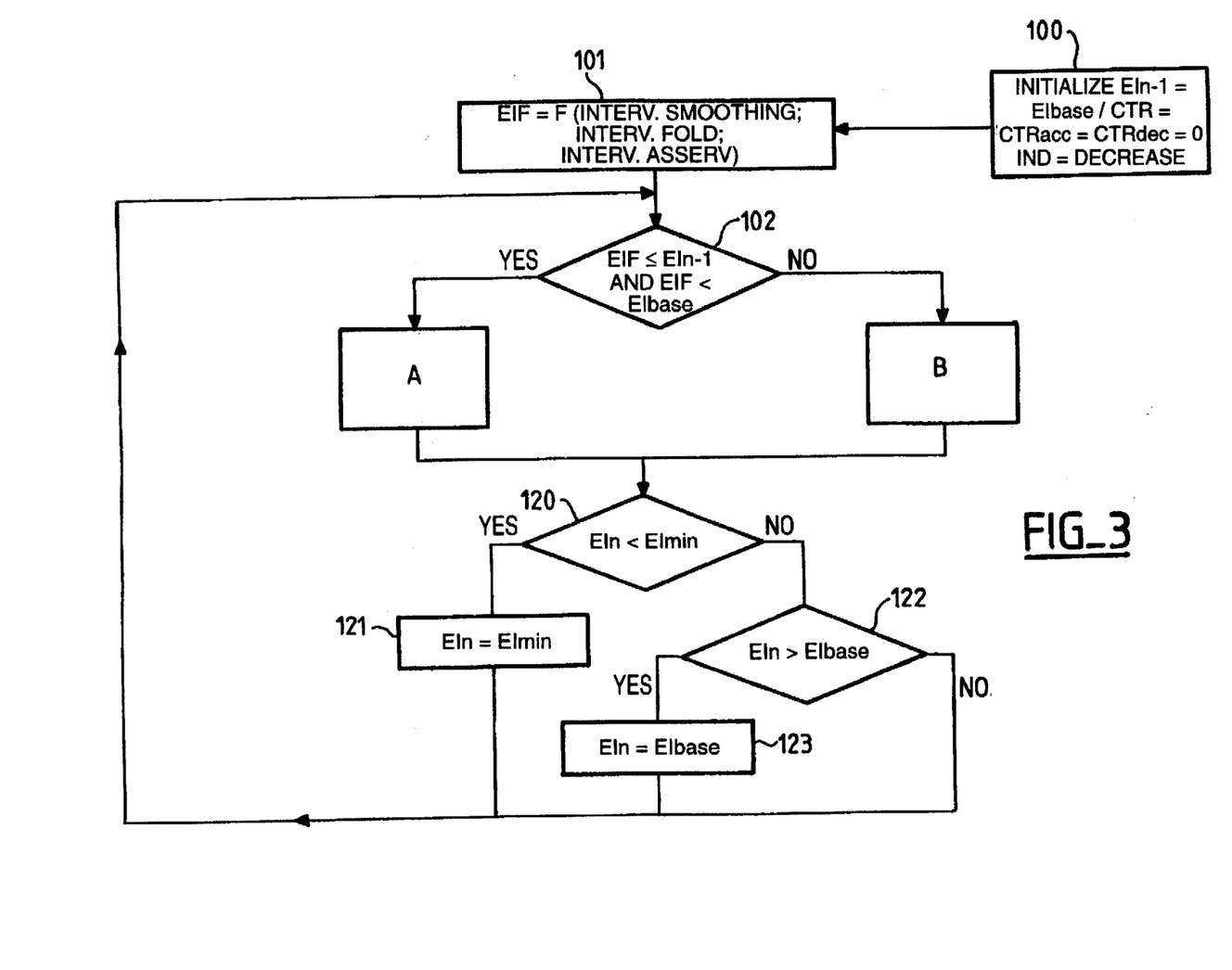
FIG. 3 is a flow chart of a general implementation of the present invention.
Figure 4:
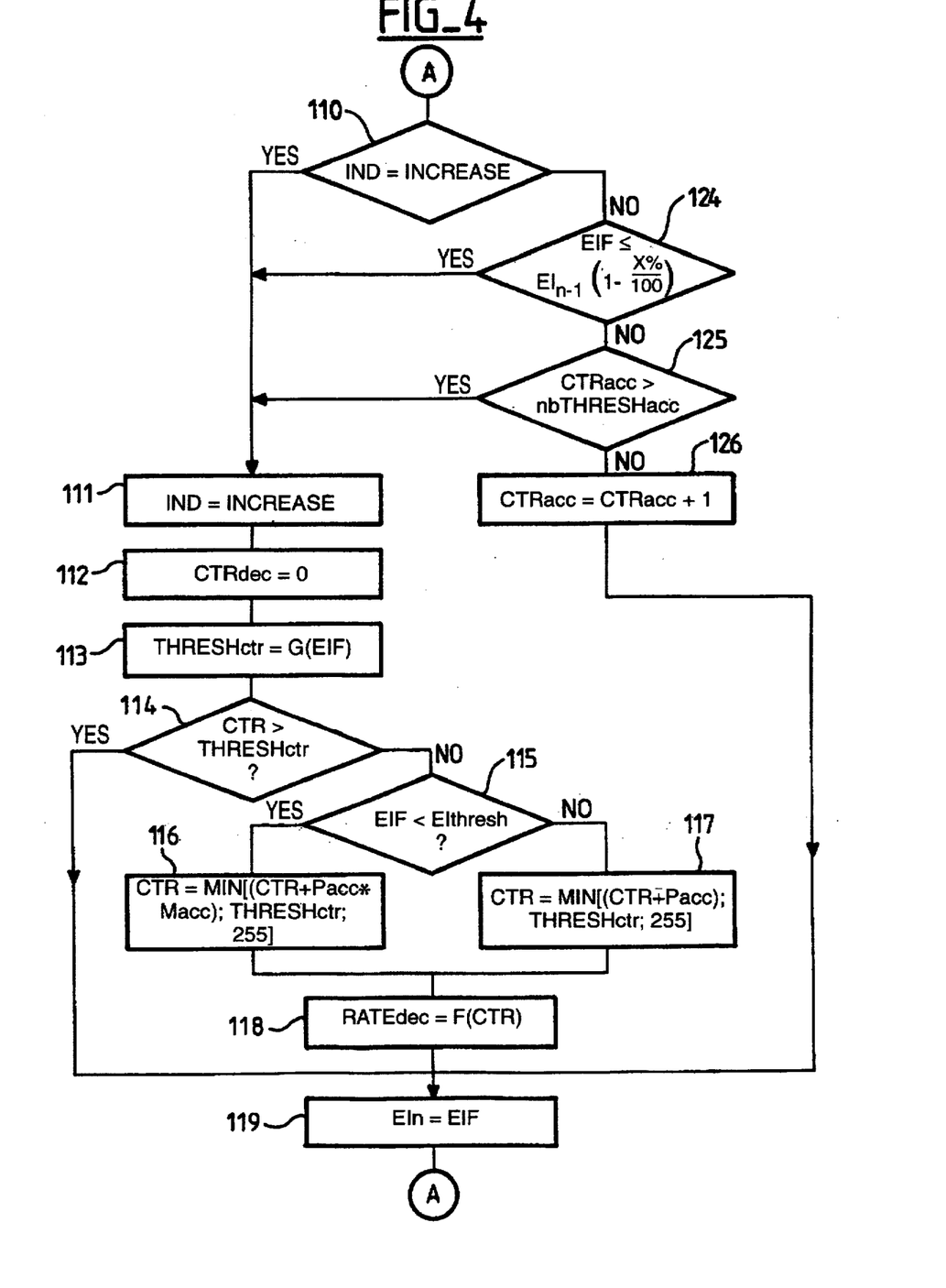
FIGS. 4 and 5 are respectively flow charts of portions A and B of FIG. 3.
Figure 5:
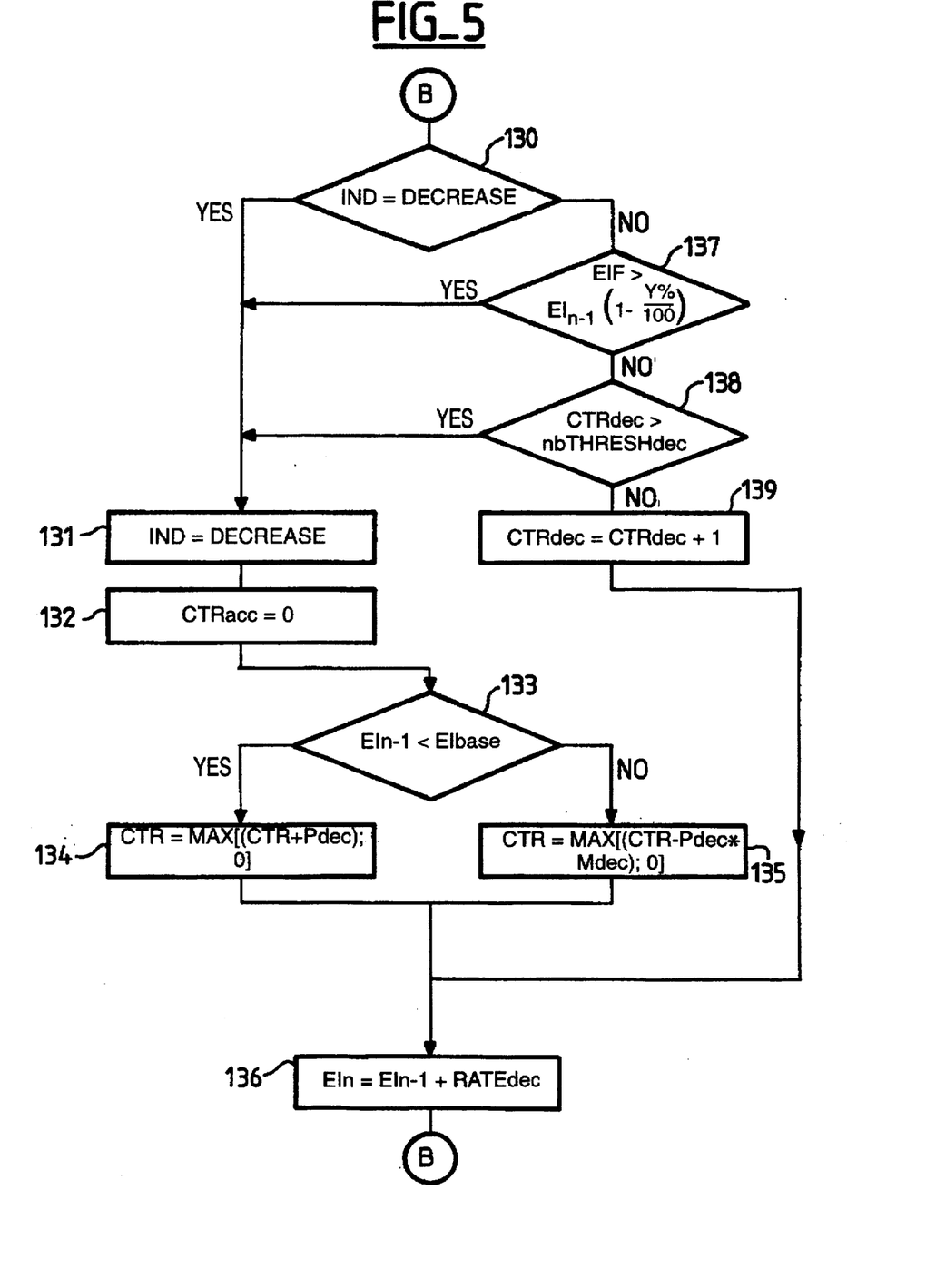

Referring to FIGS. 3–5, the counter control algorithm will be described in detail.

With reference to FIG. 3, the routine typically begins with an initialization procedure at step 100.

The Value EIn-1 is initialized to EIbase, Ind is initialized to decrease, CTRacc and CTRdec are initialized to zero, CTR is initialized to zero, and RATEdec is initialized to its slowest value.

The routine then determines the value of EIf at step 101. This value is chosen from among the different escape intervals proposed by the different algorithms available.

In a cardiac pacemaker example possessing a rate responsive function and a smoothing function, EIf will be determined by the equation:

EIf=function (interv. smoothed; interv. fold; interv. of asserv.)

wherein "interv. smooth" is the interval used in the smoothing function, "interv. fold" is the interval used to discriminate atrial extrasystoles, and "interv. asserv." is the rate responsive interval determined based on the sensor(s) 23. More precisely, when the pacemaker is in a phase of atrio-ventricular association, the chosen interval will be the smallest as between the smoothed interval and the rate responsive interval. In a phase of "fold" (that is to say in a phase of atrial ventricular dissociation), the fold escape interval will be chosen instead.

At step 102, the routine determines if the cardiac rhythm is increasing or decreasing. This task, as well as the rest of the routine, is undertaken periodically. In this application, the periodicity of the calculation is four cardiac cycles, but in other embodiments of the invention, it can be one cycle or, in a more general manner, n cardiac cycles. To determine whether or not the cardiac rhythm is increasing, the algorithm compares EIf and EIn-1 (where EIn-1 is the preceding cardiac escape interval and EIf concerns the cardiac cycle Pn).

If EIf is strictly greater than EIn−1 or greater than or equal to EIbase, a decrease of the cardiac rhythm is suspected. This is case B which will be discussed later. If on the contrary EIf is less than or equal to EIn−1 and less than EIbase, an increase of the cardiac rhythm is suspected.

In the case where an increase of the cardiac rhythm is suspected, the routine passes to case A at step 110 (FIG. 4). It tests here the state of the term Ind. If the value of Ind is increasing, then the increase of the cardiac rhythm has already been confirmed, and the routine sets Ind to the value "increase" at step 111 and sets CTRdec to zero at step 112.

The routine then manages the evolution of the counter value CTR. -At step 113, the limit value THRESHCtr is calculated as the function G and from the calculated value of EIf. This function G is the table of correspondence presented in FIG. 6.

At step 114, the value of the counter CTR is compared to its limit THRESHCtr, which is calculated at step 113.

If CTR is greater than or equal to its limit, the counter count CTR is not incremented and remains constant. The routine then passes to step 119. If on the contrary, CTR is less than THRESHCtr, the counter can be incremented. The period of increase divides in two phases, as determined by the value of EIf. This occurs in the next stage of the routine.

At step 115, the routine tests the value of EIf as compared to the EIthresh. If EIf is greater than EIthresh, at step 117 the counter takes the smaller value as between the value of the counter CTR incremented by Pacc, the THRESHCtr value determined at step 113, and the maximal value of the counter, in this example 255. If on the contrary, EIf is less than or equal to EIthresh, at step 116 the counter takes the minimal value as between the value of the counter CTR incremented by Pacc multiplied by Macc, THRESHCtr as determined at step 113, and the maximal value of the counter, in this case 255.

The value of the counter CTR thus being determined, the routine next determines the value of the rate of decrease RATEdec with the help of the function F, at step 118. This function F is the table of correspondence in FIG. 7 that associates with each counter value CTR a value RATEdec.

Figure 8:
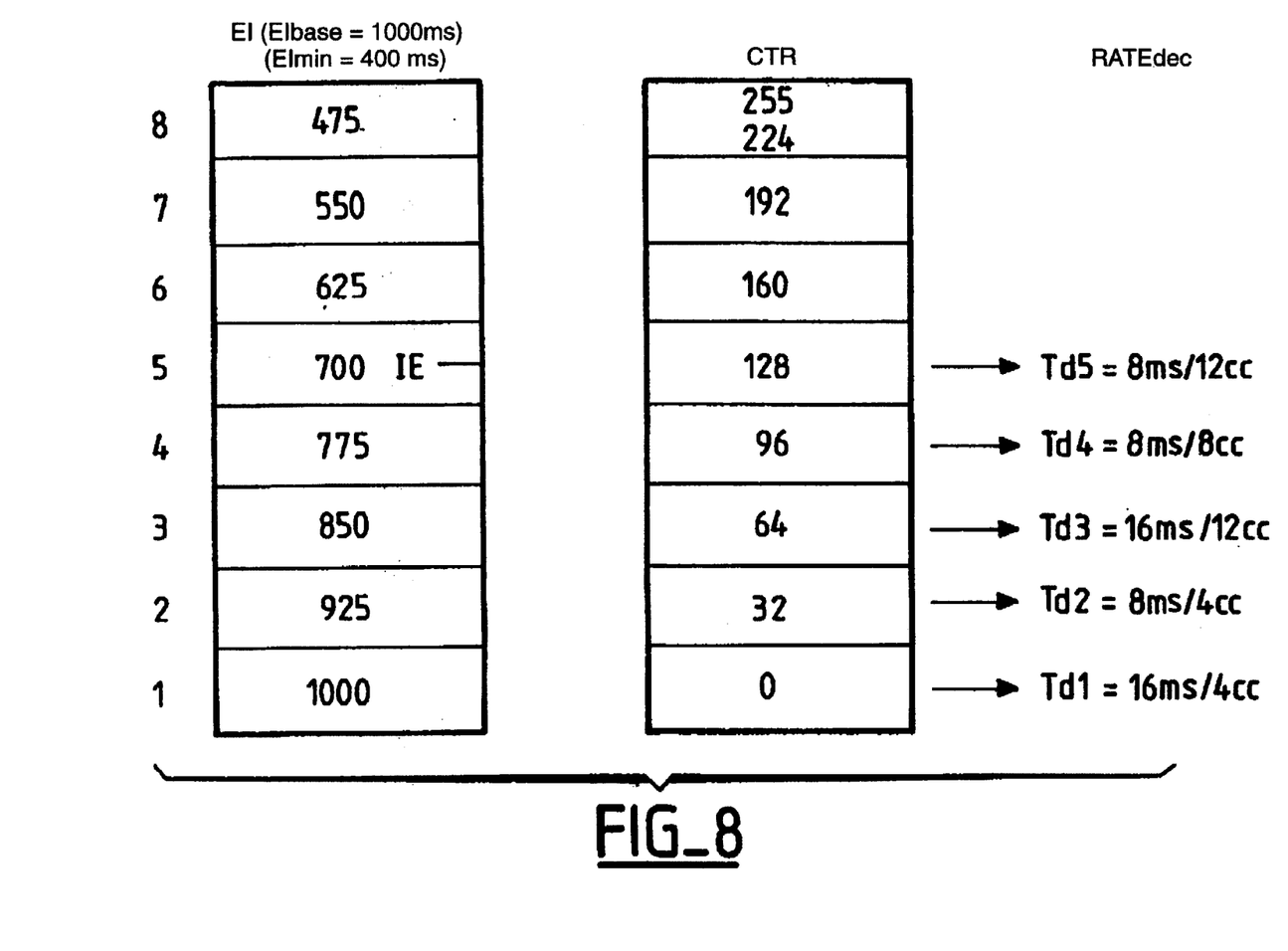
FIG. 8 is a table of correlations between periods of stimulation, value of the counter, and the rate of deceleration of the cardiac rhythm.

Referring to FIG. 8, an example of the correlation existing at a given moment between the frequency f or the cardiac period (EI), the counter value CTR and the rate of deceleration RATEdec, is shown. The interval of periods existing between EIbase and EImin is divided in eight ranges of periods of equal extent. Each range has a corresponding counter value limit THRESHCtr. Thus, for a given period in which EI is between 700 ms and 625 ms, the counter CTR limit value is 159. The counter can therefore have a value CTR between 1 and 159. In this embodiment, the 255 possible values of the counter are equally distributed in the eight ranges, but it should be understood that other distributions may be used.

In addition, each of these ranges of values has a corresponding value of the rate of decrease RATEdec. Thus, for the values of the counter available for the given EI, according to the value CTR reached by the counter, one can have one of the five rates of deceleration shown in FIG. 8, from between 16 ms/4 cc and 8 ms/12 cc.

Referring again to FIG. 4, at step 119, the routine allocates to EIn a new value (the present invention manages only periods of decrease of the cardiac rhythm; during periods of increase of the cardiac rhythm, the algorithm allocates to EIn the value of EIf).

Returning to FIG. 3, the routine undertakes then two further tests to verify that the value of EIn does not exceed the minimal value EImin and the maximal value EIbase. At step 120, EIn is compared to EImin. If EIn is less than EImin, then EIn is set equal to EImin at step 121. If EIn is greater than or equal to EImin, the routine then passes to step 122 where EIn is compared to EIbase. If EIn is greater than EIbase, then EIn is set equal to EIbase at step 123. Otherwise, EIn is used at its determined value. EIn thus represents the stimulation interval calculated for the cardiac cycle Pn.

Returning to FIG. 4, the case where, at step 110, Ind is equal to "decrease", and the increase in cardiac rhythm as suspected by comparing EIf and EIn−1 at step 102 has not been again confirmed, the routine will behave differently. Before the value of the counter is changed, the routine seeks to confirm the increase of the rhythm. At step 124, the routine realizes the first test of confirmation of the cardiac rhythm. This concerns the difference between EIn−1 and EIf. If EIf is less than a limit value which is equal to EIn−1 decreased by a hysteresis amount (an amount that is fixed arbitrarily in this embodiment to x=6.25%), then it is determined that the cardiac rhythm has significantly accelerated and the increase of the rhythm is confirmed. The routine then continues to step 111.

On the other hand, if at step 124 EIf is greater than the limit value, the increase is not confirmed and the routine passes to the second test at step 125. The test realized at step 125 is a temporization which allows for the confirmation of the increase of the rhythm, and provides for increasing a counter CTRacc. The counter CTRacc is initialized to zero during periods of decrease. When the value of counter CTRacc is greater than a threshold nbTHRESHacc, as previously defined (and fixed in this embodiment to 4), that means the routine has passed by this test nbTHRESHacc consecutive times. The increase state is then confirmed and the routine proceeds to continue from step 111.

If, on the contrary, CTRacc is less than this threshold nbTHRESHacc, the increase state is not confirmed. In such a case, at step 126, the routine increments the value of counter CTRacc, the increase is not confirmed, and the routine does not determine either the counter CTR, or RATEdec. Rather, the routine passes directly to step 119 as described previously.

In the process described above, an increase of the cardiac rhythm had been suspected at step 102. If, on the other hand, at step 102, EIf is greater than EIn−1, or if EIf is greater than or equal to EIbase, the routine detects a decrease of the cardiac rhythm and proceeds according to case B.

With reference to FIG. 5, in the case B, the value of Ind is tested at step 130. If Ind is set to decrease, that indicates that the decrease of the cardiac rhythm has already been confirmed. In such case, Ind is set to "decrease" at step 131, and the value of counter CTRacc is set to zero at step 132.

At step 133, the routine tests the value of EIn−1. If EIn−1 is less than EIbase, the decrease is not ended and the rhythm has not reached the base rhythm. At step 134, the counter value CTR is then is set to the maximal value as between the value CTR of the counter decremented by Pdec (Mdec=1) and zero.

On the other hand, if at step 133 EIn−1 is greater than or equal to EIbase, then the cardiac rhythm has returned to rest, and at step 135 the counter CTR takes the maximum value between the value CTR of the counter decremented by Pdec multiplied by Mdec (Mdec=3), and zero, to accelerate the reduction of the counter value.

Next, EIn is assigned at step 136. The present invention thus manages the decrease of the cardiac rhythm. In this regard, the algorithm uses EIn−1, the interval of the preceding cardiac escape interval and RATEdec, the last rate of decrease actualized at step 118. The routine then determines EIn to be the value of EIn−1 increased by RATEdec. The routine then proceeds according to steps 120, 121, 122 and 123 as previously described.

If, at step 130, Ind is to set the value "increase", the routine undertakes a test to confirm the decrease of the cardiac rhythm. The first test is undertaken at step 137 using EIf and EIn−1. If EIf is greater than a limit value which is EIn−1 plus a hysteresis value of y% of EIn−1 (fixed here arbitrarily to y=12.5%), the routine confirms the decrease of the rhythm, and continues as previously described from step 131.

If, however, EIf is less than this limit value based on hysteresis, the routine passes to a second test at step 138. At step 138, the routine tests the value of counter CTRdec that has been initialized to zero during periods of increase of the cardiac rhythm. This counter ranges between zero and a threshold THRESHdec. If, at step 138, the counter CTRdec is greater than nbTHRESHdec, the decrease is confirmed and the routine continues from step 131. If the counter CTRdec is still below nbTHRESHdec, the routine increases the value of counter CTRdec at step 139. Then, without adjusting the counter value CTR, the routine determines EIn to be the value of EIn−1 +RATEdec at step 136.

The hysteresis percentage y used during the period of decrease can, in an alternate embodiment, be equal to the hysteresis percentage x used to confirm the increase. The choice in this exemplary embodiment to use a larger hysteresis percentage y for the decrease is to render more severe and more selective the criterion of decrease.

It will be understood that, in accordance with the present invention, the rate of deceleration of the stimulation rhythm is thus controlled based on the preceding cardiac rhythm and determined stimulation rate information, so as to obtain a more physiological deceleration than the prior known smoothing techniques. Advantageously, the process and apparatus may be implemented in virtually any active implantable medical device for cardiac monitoring and therapy.

One skilled in the art will appreciate that the present invention can be practiced by other than the described embodiments, which are presented for purposes of illustration and not of limitation.

We claim:

1. An active implantable medical device to be borne by a patient comprising:

means for detecting an instantaneous cardiac rhythm of the patient, means for delivering stimulation pulses having an escape interval (EIn) between successive delivered stimulation pulses, and means for gradually increasing said escape interval comprising means for memorizing information corresponding to a plurality of successive detected instantaneous cardiac rhythms, wherein the gradually increasing means is operated to increase a given escape interval by a variable amount that is a first function of previously memorized information of the detected cardiac rhythm.

2. The apparatus of claim 1, wherein the gradually increasing means further comprises means for determining a rate of increase of the escape interval (RATEdec) as a second function of said memorized information, wherein the first function further operates on said determined rate of increase RATEdec.

3. The apparatus of claim 1, wherein the first function of the gradually increasing means is an integration of the previously memorized information of the detected cardiac rhythm.

4. The apparatus of claim 1, further comprising means for determining a state (Ind) of increase or decrease of the escape interval, and means for determining a rate of increase of said gradually increasing means, wherein the gradually increasing means, in response to a detected decrease state, is operated to apply the determined rate of increase to increase said escape interval and, in response to a detected increase state, is maintained at the value previously applied.

5. An active implantable medical device to be borne by a patient comprising:

means for detecting an instantaneous cardiac rhythm of the patient, means for delivering stimulation pulses having an escape interval (EIn) between successive delivered stimulation pulses, means for gradually increasing said escape interval comprising means for memorizing information corresponding to an evolution of said cardiac rhythm detected by said detecting means, wherein the gradually increasing means is operated to increase a given escape interval by a variable amount that is a first function of previously memorized information of the detected cardiac rhythm, and means for determining a rate of increase of the escape interval (RATEdec) as a second function of said memorized information, wherein the first function further operates on said determined rate of increase RATEdec.

6. An active implantable medical device to be borne by a patient comprising:

means for detecting an instantaneous cardiac rhythm of the patient, means for delivering stimulation pulses having an escape interval (EIn) between successive delivered stimulation pulses, and means for gradually increasing said escape interval comprising means for memorizing information corresponding to an evolution of said cardiac rhythm detected by said detecting means, wherein the gradually increasing means is operated to increase a given escape interval as by a variable amount that is an integration of the previously memorized information of the detected cardiac rhythm.

7. The apparatus of claim 6, further comprising a counter having a count value (CTR) and a means for determining a rate of increase of the escape interval (RATEdec), wherein the gradually increasing means operates to increase or decrease the count value CTR in response to the detected cardiac rhythm, and wherein the rate determining means determines the rate of increase (RATEdec) according to the count value (CTR), and wherein the first function further operates on said determined rate of increase RATEdec.

8. The apparatus of claim 7, wherein the rate of increase RATEdec varies inversely to the count value CTR.

9. The apparatus of claim 7, wherein the rate determining means further comprises a plurality of ranges of values, each range corresponding to a preselected rate of increase, and means for comparing the counter count value to said plurality of ranges to select a rate of increase corresponding to the count value CTR.

10. The apparatus of claim 7 further comprising a means for calculating a final escape interval value (EIf), wherein the counter count values range between a minimal limit and a maximal limit, and wherein the maximal limit is a variable that is a function of said calculated final escape interval value (EIf).

11. The apparatus of claim 7 further comprising a means for calculating a final escape interval value (EIf), further comprising means for the counter in which of incrementing the counter in which the speed of incrementing varies according to the calculated final escape interval value (EIf).

12. The apparatus of claim 8, wherein the speed determining means further compromises a multiplier factor variable (Macc) having a value according to the calculated final interval escape value (EIf).

13. The apparatus of claim 7, further comprising means for determining a speed of incrementing the counter in which the speed of incrementing varies according to the value of the escape interval determined for the preceding cardiac cycle.

14. The apparatus of claim 13, further comprising means for calculating a final escape interval value (EIf), wherein the speed determining means further comprises a multiplier factor variable (Mdec) having a value according to the calculated final escape interval value (EIf).

15. An active implantable medical device to be borne by a patient comprising:
means for detecting an instantaneous cardiac rhythm of the patient,
means for delivering stimulation pulses having an escape interval (EIn) between successive delivered stimulation, pulses, and
means for gradually increasing said escape interval comprising means for memorizing information corresponding to an evolution of said cardiac rhythm detected by said detecting means, wherein the gradually increasing means is operated to increase a given escape interval as a first function of previously memorized information of the detected cardiac rhythm,
means for determining a state (Ind) of increase or decrease of the escape interval, and
means for determining a rate of increase of said gradually increasing means, wherein the gradually increasing means, in response to a detected decrease state, is operated to apply the determined rate of increase to increase said escape interval and, in response to a detected increase state, is maintained at the value previously applied.

16. A method of controlling the escape interval of a cardiac stimulation device comprising:
(a) providing a base escape interval for stimulating a heart at a basic cardiac rhythm;
(b) monitoring cardiac electrical activity including spontaneous and stimulated cardiac events;
(c) determining an escape interval for a cardiac stimulation in the absence of a spontaneous cardiac event;
(d) determining whether the determined escape interval corresponds to an increasing cardiac rhythm or a decreasing cardiac rhythm; and
(e) in response to a determined increasing cardiac rhythm:
(i) recording a history of the increase of the cardiac rhythm, and
(ii) determining a rate of increase of an escape interval as a function of the recorded history; and
(f) in response to a determined decreasing cardiac rhythm:
(i) applying the rate of increase determined during a determined increasing cardiac rhythm preceding said determined decreasing cardiac rhythm to increase gradually the determined escape interval to the base escape interval, and
(ii) using the increased escape interval in said device.

17. The method of claim 16 wherein step (e) further comprises using said determined escape interval in the device during said determined increasing cardiac rhythm.

18. The method of claim 16 wherein step (c) further comprises determining said escape interval in response to the detected cardiac electrical activity.

19. The method of claim 18 wherein step (c) further comprises monitoring a physiological parameter indicative of a patient's cardiac output requirements, determining a rate responsive escape interval as a function of said monitored physiological parameter, and determining the escape interval as a function of the determined rate responsive escape interval and the detected cardiac electrical activity.

20. The method of claim 19 wherein step (c) further comprises smoothing the determined escape interval according to a predetermined slope.

21. The method of claim 16 wherein step (c) further comprises monitoring a physiological parameter indicative of a patient's cardiac output requirements, and determining said escape interval as a function of said monitored physiological parameter.

22. The method of claim 16 wherein step (c) further comprises selecting an escape interval according to one of a plurality of algorithms for determining an escape interval.

23. The method of claim 16 wherein step (d) further comprises:
comparing a last determined escape interval and a previously determined escape interval;
declaring that the cardiac rhythm is increasing in response to the previously determined escape interval being larger than the last determined escape interval; and
declaring that the cardiac rhythm is decreasing in response to the last determined escape interval bing larger than the preceding determined escape interval.

24. The method of claim 23 further comprising performing step (d) every n cardiac cycles, wherein n is an integer selected from between 2 and 16.

25. The method of claim 16 wherein step (d) further comprises:
(i) comparing a last determined escape interval to a previously determined escape interval and the base escape interval;
(ii) suspecting an increasing cardiac rhythm in response to one of the last determined escape interval being less than or equal to the preceding determined escape interval and the last determined escape interval being less than the base escape interval;
(iii) in response to a suspected increasing cardiac rhythm, confirming that the suspected increasing cardiac rhythm is increasing;
(iv) suspecting a decreasing cardiac rhythm in response to one of the last determined escape interval being greater than the preceding determined escape interval and the last determined escape interval being greater than or equal to the base escape interval; and
(v) in response to a suspected decreasing cardiac rhythm, confirming that the suspected decreasing cardiac rhythm is decreasing.

26. The method of claim 25 wherein step (e) does not respond to the suspected increasing cardiac rhythm that is not confirmed, and wherein step (f) does not respond to the suspected decreasing cardiac rhythm that is not confirmed.

27. The method of claim 25, wherein step (d) further comprises:
providing a first hysteresis amount and a second hysteresis amount;
(g) maintaining an indicator having a first state corresponding to a confirmed increasing cardiac rhythm and a second state corresponding to a confirmed decreasing cardiac rhythm;

wherein step (d) (iii) further comprises determining one of the indicator being in the first state, a difference between the last determined escape interval and the preceding determined escape interval decreased by the first hysteresis amount being greater than the first hysteresis amount, and the occurrence of at least a preselected number of successive attempts to confirm a suspected increasing cardiac rhythm; and wherein step (d) (v) further comprises determining one of the indicator being in the second state, a difference between the last determined escape interval and the preceding determined escape interval increased by the second hysteresis amount being greater than the second hysteresis amount, and the occurrence of at least a preselected number of successive attempts to confirm a suspected decreasing cardiac rhythm.

28. The method of claim 27 wherein step (g) (iii) further comprises setting the indicator to the first state in response to a confirmed increasing cardiac rhythm and wherein step (g) (v) further comprises setting the indicator to the second state in response to a confirmed decreasing cardiac rhythm.

29. The method of claim 16 wherein:

step (e) (i) further comprises providing a counter having a count value and incrementing the counter value in response to a determined escape interval corresponding to a determined increasing cardiac rhythm; and step (e)(ii) further comprises selecting the rate of increase as a function of the incremented counter count.

30. The method of claim 29 wherein step (f) further comprises (iii) decreasing the counter count value in response to a determined escape interval corresponding to a determined decreasing cardiac rhythm.

31. The method of claim 16 wherein step (e)(i) further comprises:

providing a counter having a count value, a lower count limit, an upper count limit, and a count threshold between the upper and lower count limits, and incrementing the counter count by a first value in response to a determined escape interval corresponding to an increasing cardiac rhythm and the count value being less than said count threshold;

incrementing the counter count by a second value in response to a determined escape interval corresponding to an increasing cardiac rhythm and the count value being greater than said count threshold, the count value being limited to a maximum of the upper count limit, the second value being greater than the first value; and step (e) (ii) further comprises selecting the rate of increase as a function of the incremented counter count.

32. The method of claim 31 wherein step (f) further comprises (iii) decreasing the counter count value by a third value in response to a determined escape interval corresponding to a determined decreasing cardiac rhythm and the count value being greater than the count threshold, and decreasing the counter count value by a fourth value in response to a determined escape interval corresponding to the base cardiac interval, the count value be limited to a minimum of the lower count limit, the fourth value being greater than the third value.

33. The method of claim 32 wherein step (e) (ii) further comprises:

providing a plurality of ranges of count values between said upper and lower limits;

associating with each one of said plurality of ranges a rate of increase;

determining the one range of count values including the incremented count value; and selecting the one rate of decrease associated with the one range.

34. The method of claim 31 wherein step (e) (ii) further comprises:

providing a plurality of ranges of count values between said upper and lower limits;

associating with each one of said plurality of ranges a preselected rate of increase;

determining the one range of count values including the incremented count value; and selecting the one preselected rate of increase associated with the one determined range.

35. The method of claim 34 further comprising selected each preselected rate of increase to have a magnitude in a range of from between a maximum rate and a minimum rate, the magnitude range of the selected preselected rates being inversely related to the magnitude of the counter count.

36. The method of claim 31 further comprising providing the second value as a multiple of the first value, and providing the fourth value and a multiple of the third value.

37. The method of claim 31 further comprising:

determining a multiplier as a function of the determined escape interval; and providing the second value as a function of the first value and the determined multiplier.

38. The method of claim 31 further comprising:

determining a multiplier as a function of the determined escape interval; and providing the fourth value as a function of the third value and the determined multiplier.

39. The method of claim 31 further comprising providing the counter upper limit as a variable function of the determined escape interval.

40. The method of claim 16 wherein step (e) (i) further comprises integrating the detected cardiac rhythm corresponding to the detected escape interval.

* * * * *

UNITED STATES PATENT AND TRADEMARK OFFICE
CERTIFICATE OF CORRECTION

PATENT NO. : 5,702,424
DATED : December 30, 1997
INVENTOR(S) : Legay et al.

It is certified that error appears in the above-identified patent and that said Letters Patent is hereby corrected as shown below:

Column 2, line 23, delete "parent's' and insert -- patent's --.
Column 2, line 67, after "means" delete "-";
Column 4, line 29, after "only" delete "-";
Column 9, line 13, delete "-At" and insert --At--;
Column 12, line 39, after "interval" delete "as";
Column 13, line 1, after "for" delete "the counter in which";
Column, 13 line 1, after "for" insert --determining a speed--;
Column 14, line 30, delete "bing" and insert --being--;
Column 16, line 30, delete "selected" and insert --selecting--.

Signed and Sealed this

Sixteenth Day of February, 1999

Attest:

Attesting Officer

*Acting Commissioner of Patents and Trademarks*